United States Patent [19]

Orth et al.

[11] Patent Number: 5,665,535
[45] Date of Patent: Sep. 9, 1997

[54] POLYPEPTIDES ENCODED BY DNA SEQUENCES DERIVED FROM THE GENOME OF THE PAPILLOMAVIRUS HPV39, ANTIBODIES THERETO, AND THEIR USE IN IN VITRO DIAGNOSIS

[75] Inventors: Gérard Orth, Sceaux, France; Christoph Volpers; Rolf E. Streeck, both of Wiesbaden, Germany

[73] Assignees: Institut National de la Sante et de la Recherche Medicale; Institut Pasteur, both of France

[21] Appl. No.: 468,057

[22] Filed: Jun. 6, 1995

Related U.S. Application Data

[62] Division of Ser. No. 74,879, filed as PCT/FR91/01053, Dec. 20, 1991.

[30] Foreign Application Priority Data

Dec. 20, 1990 [FR] France ................... 90 16044

[51] Int. Cl.⁶ .................. C12Q 1/70; C07K 1/100; C12N 7/00; A61K 39/395
[52] U.S. Cl. .................. 435/5; 435/69.3; 435/235.1; 530/350; 530/387.1; 530/388.3; 530/387.9; 530/389.4; 424/130.1; 424/186.1; 424/184.1; 536/23.72

[58] Field of Search ............... 435/5, 69.3, 235.1; 530/350, 387.1, 388.3, 387.9, 389.4; 536/23.72; 424/130.1, 186.1, 184.1

[56] References Cited

U.S. PATENT DOCUMENTS 4,983,728  1/1991  Herzog et al. ............... 536/24.32

FOREIGN PATENT DOCUMENTS

0235004A2  9/1987  European Pat. Off. .
0375555A1  6/1990  European Pat. Off. .

OTHER PUBLICATIONS

Beaudenon et al., Virology 161:374–384 (1987).
Reuter et al., J. Virol. 65(10):5564–5568 (Oct. 1991).
Volpers et al., Virology 181:419–423 (Mar. 1991).

*Primary Examiner*—Mary E. Mosher
*Assistant Examiner*—Michael C. Chen
*Attorney, Agent, or Firm*—Finnegan, Henderson, Farabow, Garrett & Dunner, L.L.P.

[57] ABSTRACT

Polypeptides encoded by genes of papillomavirus HPV39 are provided. Also provided are antibodies directed to the polypeptides, and methods for diagnosing genital neoplasias and for detecting infection by HPV39.

27 Claims, 5 Drawing Sheets

```
+6001 ACCCATTATA TAATAGACAG GATGATACTG AAAACTCACC ATTTTCATCA ACCACCAATA AGGACAGTAG GGATAATGTG TCTGTGGATT ATAAACAGAC
+6101 ACAGTTGTGC ATTATAGGCT GTGTTCCCGC CATTGGGGAG CACTGGGTA AGGGAAAGGC ATGCAAGCCC AATAATGTAT CTACGGGGGA CTGTCCTCCT
+6201 TTGGAACTAG TAAACACCCC TATTGAGGAT GGTGATATGA TTGATACTGG CTATGGAGCT ATGGACTTTG GTGCATTGCA GGAAACCAAA AGTGAGGTGC
+6301 CTTTAGATAT TTGTCAATCC ATTTGTAAAT ATCCTGATTA TTTGCAAATG TCTGCAGATG CAGTATGTTC TTCTGTTTAC GTAGGGAACA
+6401 AGTTCTGTAT AGACATTTT GGAATCGTGG TGGTATGGTG GGTGACGCCA CCAGTTATT AAGGCACAG ATATACGTGC AAACCCGGT
+6501 ATGGTATATG ACTGCCCCTC TCCAGGCGGT TCCATGGTAA CCCTGATTC TCCTGCCA AATAAGCCTT ATTGGCTACA TAAGGCACAA GGCCACAACA
+6601 TACATATGAT CTTGGCATAA CAATTATC TTAAGGAATA CAATTGTAAT GGAGACTACC ACTTTACATT ATCTACCTCT CCATACCTTC
+6701 GTTATGTCTT ATATTCACAC TTGGAACTT CCTTCTAAGT TGGAACTTC ATGAATTCC GTGGAGGAGT CGTAGTACCA CAACTGTATCT CTGTCACATT AACAACTGAT
+6801 ACCTACAGTC TGCAGCCATT ATATTTCAGG TGGAACTTTG AGGATGCTCC ACAATTGGAA ATGATTTACA ATCTATATTT TGGTAGAC ACTTAAGGGA
+6901 AAGTTTAGT TTGGAACTTG ATCAATTCCC TCCAGTACT AGGATGCTCC TTTGAAAGTT GCTAAATAA CTCTAAAGTT TGGAATGTTG ACTTAAGGCCT
+7001 GCTGACTAA CTTTCCTGTC CTCAGCTACT ATCAGTCAAA ACATCAATTG AAGAAGATC GCATGCGTA AGGCTGGCT TAGGGCCA AAAGCGGCCT
+7101 TTCCTTATGT CAGTGTATTT TATGTGTATG ACATGTCTAT TGTGTGTATA TGCAGGCAG GTATGACAGT CGCCCTACTA TCATGTGTG TGTTGTGT
+7201 CTGTGAGTTA CAGTGCCATT GTTCCCTACA CGTTTTCTCA TATAGGTCT GTAAAAACAA CCCCGGTA CCCTAAGGT GTTATTACTG ATTGCTTAA
+7301 AATTTACTCA TCAGGTGCA TCAGCAAAAA AATTTTACTT TATAGGTATG GCAACATTT ATACATAATC TATATGCCCT ACCTAAGGT GTGTTACTA CCTAATATGT
+7401 ACCACCTTTC CAGGGTGCA CTGACTAAC CATGTCTTTA CGTTTCTACA CCCTTAGGTT CGCCATTGCA TGGGCACCGA GTTGGCAGT GGGTTGAGCT ACTAGTGGAA
+7501 TTAAATAGT TCCAGTAGGT CTGACTACA ACTACTTC ATGTCTTTTA CATTTGGCAA ACCCTCCTCT AGTCGGTCT GTAACAGTTT TGCTTTTAGG CATATATTT ACTGTTTTT
+7601 GAAATAGGTT GGGCATACAT ACCTATACTT GATTCAGGAA TGTGTCTTTA ATACAAGTGA ATACAAGTTT ACACAATAGC TTATGCAACC
+7701 TTA
```

FIG. IC

FIG.2a
FIG.2b

Consensus: GGTACANNNTGTTCT
HPV16: TGTACATTGTGTCAT
HPV18: AGCACATACTATACT
HPV39 (NCR): TCTACATTTATACT
HPV39 (L1): GGGACAGTATGTTCT

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GCTGCTACAG G            11

( 2 ) INFORMATION FOR SEQ ID NO:2:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 5..8
        ( D ) OTHER INFORMATION: /N= "unknown"

( x i ) SEQUENCE DESCRIPTION: SEQ ID NO:2:

ACCGNNNNCG GT          12

( 2 ) INFORMATION FOR SEQ ID NO:3:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:3:

AAAGGGAGTA                                                                                    10

(2) INFORMATION FOR SEQ ID NO:4:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: DNA (genomic)

(ix) FEATURE:
    (A) NAME/KEY: Peptide
    (B) LOCATION: 2..3
    (D) OTHER INFORMATION: /note= "Xaa is unknown."

(xi) SEQUENCE DESCRIPTION: SEQ ID NO:4:

Cys  Xaa  Xaa  Cys
 1

(2) INFORMATION FOR SEQ ID NO:5:

(i) SEQUENCE CHARACTERISTICS:
    (A) LENGTH: 18 amino acids
    (B) TYPE: amino acid
    (D) TOPOLOGY: linear (ii) MOLECULE TYPE: peptide (ix) FEATURE:
    (A) NAME/KEY: Peptide
    (B) LOCATION: one-of(3, 4, 6, 10)
    (D) OTHER INFORMATION: /note= "Xaa is unknown."

(xi) SEQUENCE DESCRIPTION: SEQ ID NO:5:

Asp  Asn  Xaa  Xaa  Cys  Xaa  Ser  Thr  Glu  Xaa  Asp  Glu  Asp  Glu  Ser  Thr
 1                    5                         10                        15

Asp  Glu (2) INFORMATION FOR SEQ ID NO:6:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: misc_feature
    (B) LOCATION: 7..9
    (D) OTHER INFORMATION: /N= "unknown"

(xi) SEQUENCE DESCRIPTION: SEQ ID NO:6:

GGTACANNNT GTTCT                                                                              15

(2) INFORMATION FOR SEQ ID NO:7:

(i) SEQUENCE CHARACTERISTICS:

(A) LENGTH: 15 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

TCTACATTTT ATACT                                                                                           15

(2) INFORMATION FOR SEQ ID NO:8:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:8:

GGGACAGTAT GTTCT                                                                                           15

(2) INFORMATION FOR SEQ ID NO:9:

(i) SEQUENCE CHARACTERISTICS:
(A) LENGTH: 7833 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

```
CTTATAACAT TTTATAAGTA TCTTGTTTAA AAAAAGGGAG TAACCGAAAA CGGTCAGGAC        60
CGAAATCGGT GGATATAAAA CGCAGTCACA GTTTCTGTCC ATACCGATGG CGCGATTTCA       120
CAATCCTGCA GAACGGCCAT ACAAATTGCC AGACCTGTGC ACAACGCTGG ACACCACCTT       180
GCAGGACATT ACAATAGCCT GTGTCTATTG CAGACGACCA CTACAGCAAA CCGAGGTATA       240
TGAATTTGCA TTTAGTGATT TATATGTAGT ATATAGGGAC GGGGAACCAC TAGCTGCATG       300
CCAATCATGT ATAAAATTTT ATGCTAAAAT ACGGGAGCTA CGATATTACT CGGACTCGGT       360
GTATGCAACT ACATTAGAAA ATATAACTAA TACAAAGTTA TATAATTTAT TAATAAGGTG       420
CATGTGTTGT CTGAAACCGC TGTGTCCAGC AGAAAAATTA AGACACCTAA ATAGCAAACG       480
AAGATTTCAT AAAATAGCAG GAAGCTATAC AGGACAGTGT CGACGGTGCT GGACCACAAA       540
ACGGGAGGAC CGCAGACTAA CACGAAGAGA AACCCAAGTA TAACATCAGA TATGCGTGGA       600
CCAAAGCCCA CCTTGCAGGA AATTGTATTA GATTTATGTC CTTACAATGA AATACAGCCG       660
GTTGACCTTG TATGTCACGA GCAATTAGGA GAGTCAGAGG ATGAAATAGA TGAACCCGAC       720
CATGCAGTTA ATCACCAACA TCAACTACTA GCCAGACGGG ATGAACCACA GCGTCACACA       780
ATACAGTGTT CGTGTTGTAA GTGTAACAAC ACACTGCAGC TGGTAGTAGA AGCCTCACGG       840
GATACTCTGC GACAACTACA GCAGCTGTTT ATGGACTCAC TAGGATTTGT GTGTCCGTGG       900
TGTGCAACTG CAAACCAGTA ACCTGCTATG GCCAATCGTG AAGGTACAGA CGGGGATGGG       960
TCGGGATGTA ACGGATGGTT TCTAGTACAG GCAATAGTAG ATAAACAAAC AGGCGACACA      1020
GTGTCGGAGG ATGAGGATGA AAATGCAACA GATACAGGTT CAGACCTGGC AGACTTTATT      1080
GATGATTCCA CAGATATTTG TGTACAGGCA GAGCGTGAGA CAGCACAGGT ACTTTTACAT      1140
ATGCAAGAGG CCCAAAGGGA TGCACAAGCA GTGCGTGCCT TAAAACGAAA GTATACAGAC      1200
AGCAGTGGCG ACACTAGACC GTATGGAAAA AAAGTAGGCA GGAATACCAG GGGAACACTA      1260
```

```
CAGGAAATTT CATTAAATGT AAGCAGTACG CAGGCAACAC AAACGGTGTA TTCCGTGCCA    1320
GACAGCGGAT ATGGCAATAT GGAAGTGGAA ACAGCTGAAG TGGAGGAGGT AACTGTAGCA    1380
ACTAATACAA ATGGGGATGC TGAAGGGGAA CATGGCGGCA GTGTACGGGA GGAGTGCAGT    1440
AGTGTGGATA GTGCTATAGA TAGTGAAAAC CAGGATCCCA AATCTCCAAC TGCACAAATT    1500
AAATTATTGT TACAATCCAA TAACAAAAAG GCTGCAATGC TAACACAATT TAAAGAAACA    1560
TATGGACTAT CCTTTACTGA CCTGGTACGT ACGTTAAAA GTGATAAAAC AACATGTACA    1620
GACTGGGTGG CAGCCATATT TGGAGTACAT CCAACTATTG CAGAAGGATT TAAAACATTA    1680
ATCAACAAAT ATGCCTTATA TACACATATA CAAAGCTTAG ACACAAAACA AGGAGTACTA    1740
ATTTTAATGC TAATAAGATA TACATGTGGA AAAATAGGG TTACTGTAGG AAAGGGATTA    1800
AGTACATTGT TACATGTTCC AGAAAGTTGT ATGCTTCTGG AGCCTCCTAA ACTGCGCAGC    1860
CCTGTAGCAG CACTATATTG GTATCGCACA GGTATATCCA ATATTAGTGT GGTAACAGGG    1920
GATACGCCAG AATGGATACA ACGATTAACT GTTATACAAC ATGGAATAGA TGATAGTGTA    1980
TTTGACCTAT CGGACATGGT ACAATGGGCA TTTGACAATG AATATACTGA TGAAAGTGAC    2040
ATAGCATTTA ATTATGCAAT GTTAGCAGAT TGTAACAGTA ATGCTGCAGC CTTTTTAAAA    2100
AGTAACTGCC AGGCAAAATA TGTAAAAGAT TGTGCAACAA TGTGTAAACA TTACAAGCGA    2160
GCACAAAAAA GGCAAATGTC CATGTCTCAA TGGATAAAAT TTAGGTGTAG TAAATGTGAT    2220
GAAGGCGGGG ACTGGAGACC CATAGTACAA TTCTTAAGAT ATCAAGGAAT AGAATTTATA    2280
TCCTTTTTAT GTGCATTAAA GGAATTTTTA AAGGGTACTC CCAAAAAAAA CTGTATAGTT    2340
ATATATGGAC CTGCGAATAC AGGAAAGTCA CATTTTGTA TGAGCCTTAT GCATTTTTA    2400
CAGGGCACAG TTATTTCATA TGTAAACTCC ACCAGCCACT TTGGCTAGA ACCACTTGCA    2460
GATGCAAAAC TAGCAATGTT AGATGATGCA ACCGGTACCT GCTGGTCATA TTTCGATAAT    2520
TATATGAGAA ATGCATTAGA TGGGTATGCA ATAAGTTTAG ATAGGAAATA TAAAAGTTTA    2580
CTACAAATGA AATGTCCACC ATTATTAATA ACCTCCAATA CCAATCCTGT GGAAGACGAT    2640
AGGTGGCCAT ATTTACGTAG TAGGCTAACA GTGTTTAAAT TCCTAATGC ATTTCCATTT    2700
GACCAAAACA GGAATCCAGT GTACACAATC AATGATAAAA ACTGGAAATG TTTTTTTGAA    2760
AAGACTTGGT GCAGATTAGA CTTGCAGCAG GACGAGGATG AAGGAGACAA TGATGAAAAC    2820
ACTTTCACAA CGTTTAAATG TGTTACAGGA CAAAATACTA GAATACTATG AACAAGACAG    2880
TAAATCAATA TATGATCAAA TTAATTATTG GAAATGTGTG CGAATGGAAA ATGCAATATT    2940
TTATGCAGCA CGAGAACGTG GCATGCATAC TATTGACCAC CAGGTGGTGC CAACCATAAA    3000
CATTTCAAAA TGTAAAGCAT ATCAAGCTAT TGAACTGCAG ATGGCACTAG AAAGTGTTGC    3060
ACAAACTGAA TACAATACAG AGGAGTGGAC ATTAAAAGAC ACTAGTAATG AACTGTGGCA    3120
TACACAGCCA AAACAATGTT TTAAAAAACA AGGAACTACA GTGGAGGTGT GGTATGATGG    3180
GGACAAATGT AATGCTATGA ACTATGTATT ATGGGGTGCT ATATATTATA AAATAATAT    3240
AGACATATGG TGTAAAACAG AAGGGTGTGT GGACTATTGG GGTATATATT ATATGAACGA    3300
GCACCTAAAA GTATACTATG AAGTGTTTAT TCAAGATGCG AAAGGTATG GGACTAGTGG    3360
CAAATGGGAA GTGCATTATA ATGGCAACAT AATTCATTGT CCTGACTCTA TGTGCAGTAC    3420
CAGTGACGGA TCGGTACCCA CTACTGAACT TACTACCGAA TTATCAAACA CCACCGCGAC    3480
CCATTCCACC GCAACAACCC CATGCACCCA AAAAACAATC CCGCCGCCGT CTCGAAAGCG    3540
ACCTCGACAG TGTGCAGTCA CAGAGCCCAC TGAGCCCGAC GGAGTGTCCC TGGACCATCT    3600
TAACAACCCA CTCCACAGTA ACAGTACAGG CCACAACACA AGACGGTACC TCAGTTGTGG    3660
```

```
TAACACTACG CCTATAATAC ATTTAAAAGG TGACAAAAAT GGTTTAAAAT GTTTAAGATA   3720
TAGACTACAA AAATATGACA CATTGTTTGA AAATATTTCA TGTACCTGGC ATTGGATACG   3780
GGGTAAGGGA ACCAAAAACG CTGGCATATT AACTGTTACA TATGCCACAG AGTCACAACG   3840
CCAAAAATTT TTGGACACTG TTAAATACC  TTCTAGTGTA CATGTTTCAT TGGGTTACAT   3900
GACATTGTAA AGTATACTAT GGATATTGTG TATGTATATT GTACATAC   TACATAGATG   3960
ATATTATTGG TATTTTTGGT GTGGTTGGT  GTGTGTATAT ATATATGTTG CAATGTCCCG   4020
CTTTTGCCGT CTGTGCATGT GTGTGCGTAT GTGTGGATAA TTGTGTTTGT GTTATTCTT    4080
ATACGTACCA CACCATTGGA GGTGTTTTT  GTATATTTAC TATTTTTTGT ATTGCCCATG   4140
TGGTTGTTGC ATAGACTGGC AATGGATATG ATATAGTACT GTATATGTAT GTGCATTGTG   4200
CATAACTACT GTACATAGCT TTTTATATTT TTTTTGTTA  CTAATAAACA TGGTTTCCCA   4260
CCGTGCTGCC AGGCGTAAGC GTGCATCTGC AACTGACCTA TATAGAACCT GTAAACAATC   4320
GGGTACCTGT CCACCAGACG TTGTTGATAA AGTTGAGGGT ACTACACTTG CTGACAAAAT   4380
TTTACAGTGG ACTAGTTTAG GTATATTTT  GGGTGGGTTA GGCATAGGCA CAGGTACTGG   4440
TACTGGGGGA CGCACAGGAT ATATACCCCT GGGGGGTAGG CCTAATACTG TTGTAGATGT   4500
GTCTCCTGCA CGTCCACCTG TAGTTATTGA ACCTGTTGGT CCTTCTGAGC CATCTATTGT   4560
GCAATTGGTG GAGGACTCAA GTGTTATAAC CTCTGGAACA CCAGTACCAA CATTTACAGG   4620
CACCTCTGGA TTTGAAATTA CTTCTTCTTC TACTACTACG CCTGCGGTAT TGGATATTAC   4680
ACCCTCCTCT GGGTCTGTAC AAATAACCTC TACTAGTTAT ACTAACCCTG CCTTTACGGA   4740
TCCTTCCTTA ATTGAGGTTC CCCAAACAGG TGAAACCTCG GGTAATATAT TTGTCAGTAC   4800
CCCTACATCA GGTACACATG GCTATGAGGA AATACCTATG GAAGTGTTTG CCACACATGG   4860
CACAGGTACC GAACCTATTA GCAGCACACC TACACCTGGA ATCAGTCGTG TGGCAGGACC   4920
ACGTTATAT  AGTAGAGCAC ATCAGCAGGT TCGTGTTAGT AATTTTGATT TTGTAACTCA   4980
CCCTTCATCA TTTGTAACAT TTGATAATCC TGCTTTTGAG CCTGTTGATA CTACATTAAC   5040
ATATGAAGCT GCTGACATAG CTCCAGATCC GGATTTTCTG GACATTGTTC GTTACATAG   5100
GCCTGCCTTA ACCTCGCGTA AGGAACAGT  AAGGTTTAGT AGGCTTGGCA AAAAGGCTAC   5160
CATGGTTACC CGGCGTGGCA CACAAATTGG AGCGCAAGTA CATTATTACC ATGACATTAG   5220
TAGTATTGCT CCTGCTGAAA GCATTGAATT ACAGCCCCTA GTTCACGCTG AGCCCTCTGA   5280
TGCTTCAGAT GCATTATTTG ATATATATGC TGATGTGGAC AATAACACAT ATTTAGATAC   5340
TGCATTTAAT AATACAAGGG ATTCGGGCAC TACATATAAC ACAGGCTCAC TACCTTCTGT   5400
GGCTTCTTCA GCATCTACTA AATATGCCAA TACAACTATT CCTTTTAGTA CCTCATGGAA   5460
TATGCCTGTA AATACTGGTC CTGATATTGC TTTACCAAGT ACTACTCCAC AGTTGCCATT   5520
GGTGCCTTCT GGACCAATAG ACACAACATA TGCAATAACC ATTCAGGGTT CCAATTATTA   5580
TTTGTTGCCA TTATTGTATT TTTTCCTAAA AAAACGTAAA CGTATTCCCT ATTTTTTTC    5640
AGATGGCTAT GTGGCGGTCT AGTGACAGCA TGGTGTATTT GCCTCCACCT TCTGTGGCGA   5700
AGGTTGTCAA TACTGATGAT TATGTTACAC GCACAGGCAT ATATTATTAT GCTGGCAGCT   5760
CTAGATTATT AACAGTAGGA CATCCATATT TTAAAGTGGG TATGAATGGT GGTCGCAAGC   5820
AGGACATTCC AAAGGTGTCT GCATATCAAT ATAGGGTATT TCGCGTGACA TTGCCCGATC   5880
CTAATAAATT CAGTATTCCA GATGCATCCT TATATAATCC AGAAACACAA CGTTAGTAT    5940
GGGCTTGTGT AGGGGTGGAG GTGGGCAGGG GCCAGCCATT GGGTGTTGGT ATTAGTGGAC   6000
ACCCATTATA TAATAGACAG GATGATACTG AAAACTCACC ATTTTCATCA ACCACCAATA   6060
```

| | | | | | | |
|---|---|---|---|---|---|---|
|AGGACAGTAG|GGATAATGTG|TCTGTGGATT|ATAAACAGAC|ACAGTTGTGC|ATTATAGGCT|6120|
|GTGTTCCCGC|CATTGGGGAG|CACTGGGGTA|AGGGAAAGGC|ATGCAAGCCC|AATAATGTAT|6180|
|CTACGGGGA|CTGTCCTCCT|TTGGAACTAG|TAAACACCCC|TATTGAGGAT|GGTGATATGA|6240|
|TTGATACTGG|CTATGGAGCT|ATGGACTTTG|GTGCATTGCA|GGAAACCAAA|AGTGAGGTGC|6300|
|CTTTAGATAT|TTGTCAATCC|ATTTGTAAAT|ATCCTGATTA|TTTGCAAATG|TCTGCAGATG|6360|
|TGTATGGGGA|CAGTATGTTC|TTCTGTTTAC|GTAGGGAACA|ACTGTTTGCA|AGACATTTTT|6420|
|GGAATCGTGG|TGGTATGGTG|GGTGACGCCA|TTCCTGCCCA|ATTGTATATT|AAGGGCACAG|6480|
|ATATACGTGC|AAACCCCGGT|AGTTCTGTAT|ACTGCCCCTC|TCCCAGCGGT|TCCATGGTAA|6540|
|CCTCTGATTC|CCAGTTATTT|AATAAGCCTT|ATTGGCTACA|TAAGGCCCAG|GGCCACAACA|6600|
|ATGGTATATG|TTGGCATAAT|CAATTATTTC|TTACTGTTGT|GGACACTACC|CGTAGTACCA|6660|
|ACTTTACATT|ATCTACCTCT|ATAGAGTCTT|CCATACCTTC|TACATATGAT|CCTTCTAAGT|6720|
|TTAAGGAATA|TACCAGGCAC|GTGGAGGAGT|ATGATTTACA|ATTTATATTT|CAACTGTGTA|6780|
|CTGTCACATT|AACAACTGAT|GTTATGTCTT|ATATTCACAC|TATGAATTCC|TCTATATTGG|6840|
|ACAATTGGAA|TTTTGCTGTA|GCTCCTCCAC|CATCTGCCAG|TTTGGTAGAC|ACTTACAGAT|6900|
|ACCTACAGTC|TGCAGCCATT|ACATGTCAAA|AGGATGCTCC|AGCACCTGAA|AAGAAAGATC|6960|
|CATATGACGG|TCTAAAGTTT|TGGAATGTTG|ACTTAAGGGA|AAAGTTTAGT|TTGGAACTTG|7020|
|ATCAATTCCC|TTTGGGACGT|AAATTTTTGT|TGCAGGCCAG|GGTCCGCAGG|CGCCCTACTA|7080|
|TAGGTCCCCG|AAAGCGGCCT|GCTGCATCCA|CTTCCTCGTC|CTCAGCTACT|AAACACAAAC|7140|
|GTAAACGTGT|GTCTAAATAA|TGCATGTGTA|TGCCTTGTTA|TGTGTGTGTA|TGTTGTTTGT|7200|
|TTCCTTATGT|GTTGAGTGTA|TATGTGTATG|TTTGTAGGTA|TGTGTGTATA|TGTTTTTGTT|7260|
|AATAAAGTAT|GTATGACAGT|TTCATGTGTG|ATTGCACACC|CTGTGACTAA|CAGTGTATTT|7320|
|GTTTTACATA|TAATAGGTCT|GCAACATTTC|ATACATAATC|TATATGCCCT|ACCCTAAGGT|7380|
|GTGTTACTA|CCTAATATGT|AATTTTTACA|TTGTTGTATG|CGTTTCTACA|TTTTATACTT|7440|
|CGCCATTTTG|TGGCGACCGA|AGTCGGTCGT|GGGTTGAGCA|TTTTTTTTAA|ACTAGTGGAA|7500|
|ACCACCTTTC|TCAGCAAAAA|CATGTCTTTA|CCTTAGGTTC|ACCCTGCATA|GTTGGCACTG|7560|
|GTAACAGTTT|TACTGGCGCG|CCTTATTACT|CATCATCCTG|TCCAGGTGCA|CTGCAACAAT|7620|
|ACTTTGGCAA|CATCCATATC|TCCACCCTAT|GTAATAAAAC|TGCTTTTAGG|CATATATTTT|7680|
|AGCTGTTTTT|ACTTGCTTAA|TTAAATAGTT|GGCCTGTATA|ACTACTTTTT|GATTCAGGAA|7740|
|TGTGTCTTAC|AGTATAAGTT|ATACAAGTGA|CTAATGTAGC|ACACAATAGT|TTATGCAACC|7800|
|GAAATAGGTT|GGGCATACAT|ACCTATACTT|TTA| | |7833|

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

TGTACATTGT GTCAT        15

( 2 ) INFORMATION FOR SEQ ID NO:11:

( i ) SEQUENCE CHARACTERISTICS:

```
( A ) LENGTH: 15 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

AGCACATACT ATACT                                                                    15
```

POLYPEPTIDES ENCODED BY DNA SEQUENCES DERIVED FROM THE GENOME OF THE PAPILLOMAVIRUS HPV39, ANTIBODIES THERETO, AND THEIR USE IN IN VITRO DIAGNOSIS

This is a division of application Ser. No. 08/074,879, filed as PCT/FR91/01053 Dec. 20, 1991.

FIELD OF THE INVENTION

The invention relates to specific DNA sequences derived from the genome of the papillomavirus HPV39, including the sequence corresponding to its entire genome as well as recombinant DNAs, in particular vectors containing these DNA sequences. The invention also relates to the cell cultures transformed with the said recombinant DNAs under conditions making it possible for them to express the corresponding sequences derived from the HPV39 genome in the form of the corresponding proteins. Finally, the invention relates to the purified proteins obtained from these cell cultures. Finally, the invention relates to the production of the immunogenic compositions containing such proteins or protein fragments.

The remainder of the report will be presented with reference to the appended figures, the legends to which are as follows:

FIG. 1: (SEQ ID NO: 9) Nucleotide sequence of the DNA strand of HPV39 analogous to the mRNA.

BACKGROUND OF THE INVENTION

The invention is based on the discovery of specific sequences present in HPV39 (SEQ ID NO: 7), (SEQ ID NO: 8), sequences which constitute its originality and which make possible particularly discriminating detection of papillomaviruses of the HPV39 type. These sequences or fragments of these sequences can be used for constituting particularly sensitive hybridization probes, in particular, primers which make possible analyses by the so-called PCR method. Before proceeding further with the description of these sequences or sequence fragments, it is proposed to make a brief review of the state of the art and, then, to provide a detailed description of the genome of HPV39.

Among the 60 if not more different types of human papillomaviruses, some are associated with neoplasias or with carcinomas of the genital apparatus (1). The DNA of HPV16 and HPV18 were detected in 50% and 20% of the biopsies of cervical, vulvar or penile cancer (2,3). The HPV 31, 33, 35, 39 and 45 were encountered less frequently in such lesions (1, 4). By using the DNA of HPV6 as a hybridization probe under conditions of low stringency, HPV39 was first cloned from biopsy samples of Bowenoid penile papules, which contain the viral DNA in its episomal form. On the other hand, the viral DNA was found to be integrated into the cellular genome of invasive carcinomas (5). In a recent study performed on 365 patients infected with HPV, the DNA of HPV39 was detected in 3.9% of the tissue samples.

The biological study of HPV has been hindered by the absence of a tissue culture system for in vitro viral propagation. The analysis of the sequence of a certain number of papillomavirus genomes (2, 3, 6–14) has provided the basis for the understanding of their genetic organization and their regulation, for the expression of individual genes and the generation of antisera, and for the evaluation of the phylogenetic relationships among the very many types of HPV.

BRIEF DESCRIPTION OF THE DRAWING

FIG. 1: Nucleotide sequence of the DNA strand of HPV39 analogous to the mRNA. Position 1 on the circular genome was determined by alignment with HPV16 and 18.

FIG. 2: Distribution of the start codons (bars above the line) and stop codons (bars below the line) in the three reading frames of the two strands of HPV39 DNA. (a) strand analogous to the mRNA, (b) complementary strand. The ORFs in (a) were identified by comparison with other types of HPV. The numbering is in agreement with that shown in FIG. 1.

DESCRIPTION OF THE PREFERRED EMBODIMENTS

Figures 3, 4:
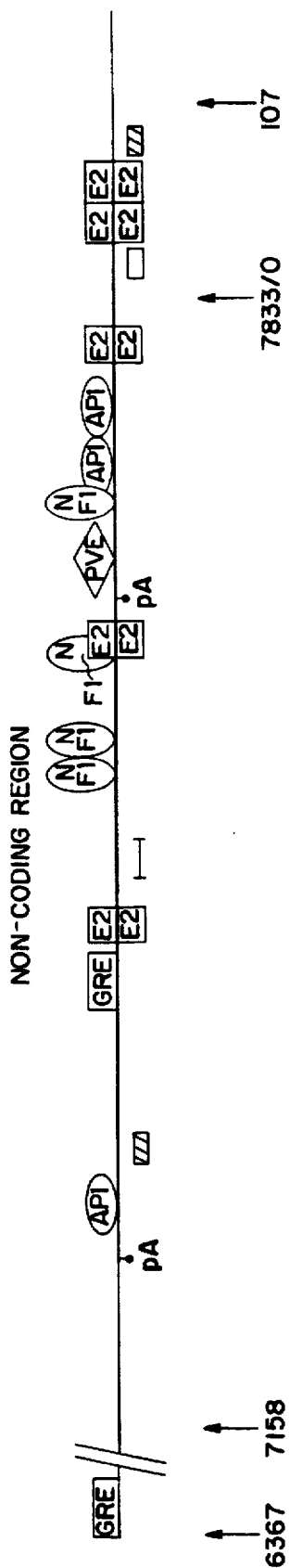
FIG. 3: Principal characteristics of the non-coding region. The following sequence motifs of the NCR are shown from the nucleotide 7158 to the nucleotide 106: ▯ represents the palindrome of 12 bp specific for the papillomavirus (the second and third motifs are degenerate). pA represents the polyadenylation site, ▮ represents the TATA box, ▭ represents the presumed promoter element, [GRE] represents the element of glucocorticoid response, ⁓ represents the core enhancer sequence, ⊛ represents the probable binding site of the nuclear factor I, (AP1) represents the presumed binding site of the activating protein 1, ◇ represents the binding site for the factor associated with the papillomavirus enhancer.
FIG. 4: Comparison of the probable elements of glucocorticoid response (GREs) of HPV39 (SEQ ID NO: 7), (SEQ ID NO: 8)compared with the GREs of HPV16 (SEQ ID NO: 10)and 18 (SEQ ID NO: 11) with a GRE/PRE consensus sequence. The nucleotides identical with the consensus sequence are underlined.

The complete nucleotide sequence of the HPV39 genome has been determined. HPV39 DNA isolated from the original clone (5) was subcloned into pUC18 in three fragments of similar size by using the unique EcoRI site and the two BamHI sites. Clones suitable for the sequencing of a DNA strand were generated by creating detection series with the aid of the exonuclease III according to the procedure of Henikoff (15). The second strand was sequenced by using synthetic oligonucleotides complementary to the first strand as primers. The sequencing of the double-stranded plasmid was performed by using the dideoxy chain termination method of Sanger et al. (16, 17).

Figure 1A:
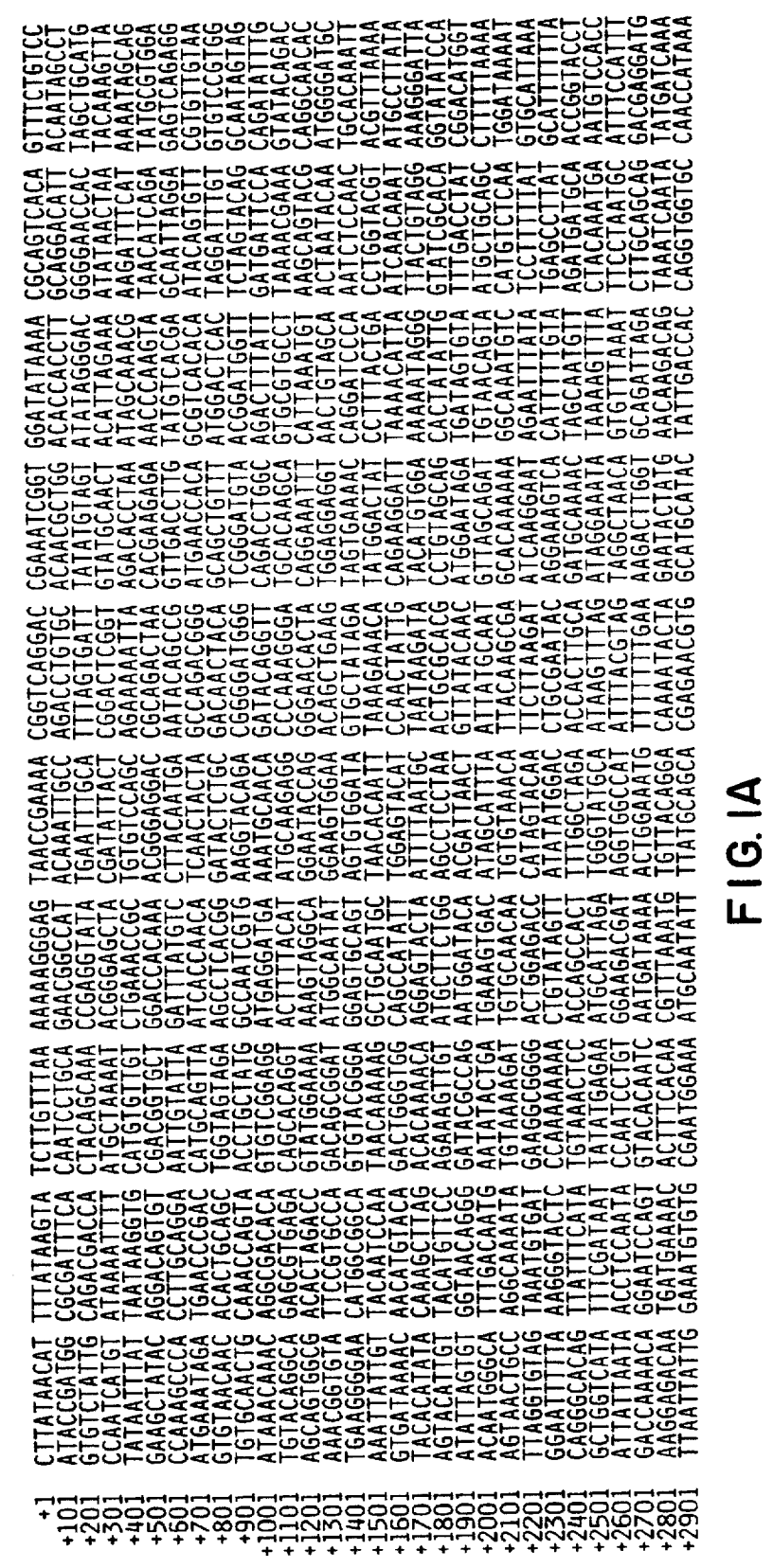

The DNA of HPV39 comprises 7833 bp (FIG. 1) and exhibits a G/C content of 40%. The restriction map derived from the sequence was confirmed by digestion of the DNA. It is in agreement with the restriction map published by Beaudenon et al.(5), with the exception of an additional HindII site, an additional PvuII and four additional AvaII sites. A AvaII site (at position 3592) is resistant to cleavage after cloning in E.coli on account of an overlapping with the recognition sequence for the dcm methylase of E. coli.

HPV39 exhibits a set of open reading frames (ORFs) conserved in all of the HPVs sequenced hitherto (FIG. 2a, Table 1). The ORFs coding for the supposed early proteins and for the components of the capsid are localized on the same DNA strand; they are separated by a non-coding region (NCR) of 782 base pairs (bp). The genomic characteristics shared by HPV39 with other genital papillomaviruses are shown by the overlappings between the ORFs E1 and E2, L2 and L1, the inclusion of E4 within E2, the localization of E7 immediately upstream from E1 (3) and the absence of the initiation codon ATG in E4, as was previously described for HPV16, 31 and 33 (2, 4, 12).

The DNA strands complementary to all of the genomes sequenced hitherto do not contain ORFs exceeding a size of 0.6 to 0.8 kb. The functional meaning of such ORFS was disproved by the absence of any detectable regulatory sequence. Furthermore, it has not been possible to demonstrate that they were transcribed in cells transformed by HPV or infected by BPV (7, 9, 18, 19). One large ORF of 1.3 kb has now been found in this DNA strand of HPV39 (nucleotides 2050–776), which includes a ATG codon and a potential acceptor splicing site (GCTGCTACAGG,(SEQ ID NO: 1) nucleotides 1871–1861) close to the 5' end (FIG. 2b). Further upstream on the same DNA strand, a minor ORF (nucleotides 4204–3875) is preceded by a TATA sequence at a distance of 23 bp (nucleotide 4227) and a binding site for the nuclear factor I (nucleotide 4271) (20, 21). At the 3' end of the ORF of 1.3 kb, a AATAAA polyadenylation signal (nucleotide 411) might be used for the maturation of a primary transcription product (22). Further experiments ought to make it possible to know whether this ORF is transcribed in vivo.

The non-coding region of HPV39 is divided into three segments by three complete versions and two degenerate versions of the palindrome ACCGNNNNCGGT (SEQ ID NO:2) specific for the papillomaviruses (nucleotides 43, 59, 7456, 7625, 7798), an E2-dependent enhancer motif (23, 24). These segments correspond to sections of similar size in the genomes of HPV16, 18 and 33 (3). There are two TATA box sequences in the non-coding region, one of them being localized upstream from the ORF E6. This latter probably constitutes a part of the E6 promoter and other early genes in association with a conserved promoter AAAGGGAGTA (SEQ ID NO: 3)placed upstream from the tandem-repeated sequences of the palindrome of 12 bp (25–27). The presumed polyadenylation site for the products of late viral transcription is localized at a site situated at about 100 base pairs downstream from the stop codon L1. Another AATAAA element situated downstream from the E5 ORF might serve as polyadenylation signal for the products of early transcription (18).

The long control regions of the previously sequenced genital HPVs contain binding sites for many transcription factors and were presented as functioning as specific enhancers of the cellular type for HPV6, 11, 16 and 18 (28–30). The regulatory region of HPV39 contains four possible binding sites for the nuclear factor I (NFI) (21, 31), two for the activation protein 1 (AP1) (21, 32), a binding motif for "the factor associated with the papillomavirus enhancer" recently described (papillomavirus enhancer associated factor: PVF) (31), and one "core enhancer sequence" conserved in SV40 and in other viruses (33) (FIG. 3). A potential element involved in the glucocorticoid response (glucoprotein response element: GRE) resembles those which are found in the NCRs of related HPV types (27). An additional highly conserved GRE element found in the ORF (nucleotide 6367) has no equivalent in other types of HPV (FIG. 4). It overlaps with an AP2 binding site that it is also found in the enhancers of SV40 and BPV (34). That indicates the presence of a regulatory function for the region situated upstream from the NCR. A cooperative effect of NFI and AP1, as well as of NPI with the glucocorticoid receptor respectively has been described for the enhancer of HPV16 (30). The interaction of many factors with potential binding sites in the NCR and in L1 of HPV39 has still to be elucidated. Donor (nucleotide 233) and acceptor (nucleotide 408) splicing sites are localised downstream from the NCR. They were demonstrated to be important for the generation of the E7 mRNA in the oncogenic types of HPV (4, 35).

Comparisons of individual ORF sequences indicate that HPV39 has the highest degree of homology with HPV18. It is more distantly related to other genital papillomaviruses, and less still with a member of the cutaneous types of HPVs, HPV8 (Table 2). Thus HPV39 belongs to a subgroup of genital HPVs exhibiting a considerable oncogenic potential which includes HPV18, HPV45(1) and a novel type showing a strong homology with HPV39 recently cloned from a cell line of the carcinoma ME180 distinct from the HPV16/31/33 group.

The ORFs E6 and E7 are usually transcribed in the cell lines of the cervical cancer and carcinoma (36), and the products of their genes are implicated in the immortalization and transformation of primary epithelial cells and fibroblasts (37). Four Cys-X-X-Cys (SEQ ID NO: 4) motifs in the E6 protein of all of the sequenced papillomaviruses, which might be implicated in the binding of DNA as a result of the formation of structures of the "zinc finger" type (38), are also present in HPV39 on the other hand, only the first of the two well-conserved Cys-X-X-Cys (SEQ ID NO: 4) elements can be found in the E7 protein. The second element has a cysteine substituted by a tyrosine. Since the mutational analysis of the ORF E7 of HPV16 has made it possible to demonstrate that one "zinc finger" is sufficient for transformational capacity (39), the E7 protein of HPV39 probably remains functional. Furthermore, the E7 protein of HPV39 contains a "cell division protein (cd)" motif which is common to many products of genes implicated in transformation, such as the T antigen of SV40, E1A of adenovirus, the myc protein and the E7 proteins of the malignant genital HPVs, but not of HPV6 or HPV11 (4): asp/asn-x-x-cysx-ser/thr/glu-x-(1–8)-aspglu-asp/glu/ser/thr-asp/glu(SEQ ID NO: 5) (the amino acids of E7 of HPV39 are underlined). The cd motifs of the large T antigen of SV40 and of the protein of the adenovirus seem to be responsible for the binding of the anti-oncogenic product of the retinoblastoma (40). The transformational activity of E7 may also be attributable to a protein-protein interaction via the cd sequence.

Figure 1B:
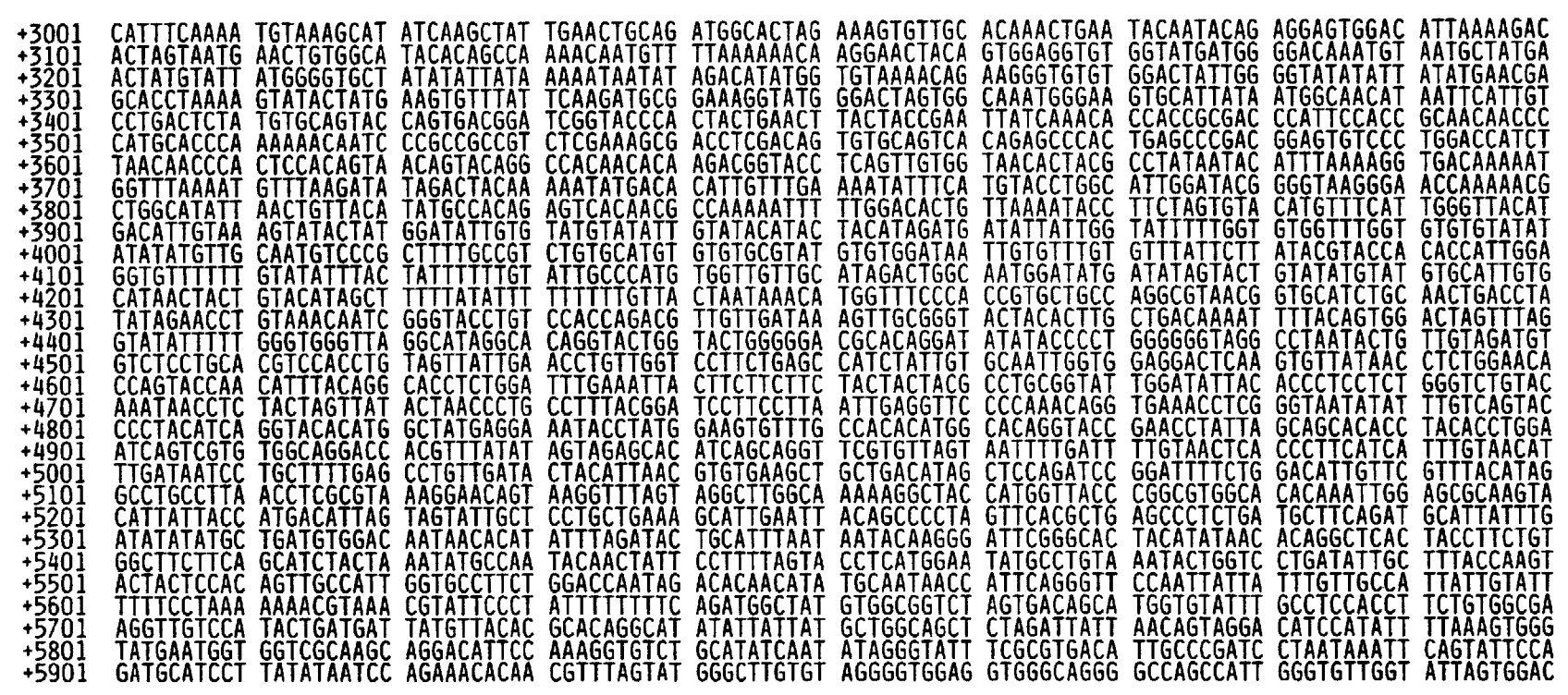

The invention relates more particularly to the sequence corresponding to the large ORF of 1.3 kb extending from the nucleotide 2050 to the nucleotide 776 of FIG. 1 or to any fragment contained in this sequence or which may be derived from it, this fragment containing at least 15 nucleotides.

The invention also relates even more particularly to the sequence corresponding to the minor ORF extending from nucleotide 4204 to nucleotide 3875 and even from nucleotide 4227 to nucleotide 3875 or sequences derived from these latter.

Similarly the invention also relates to sequences of at least 15 nucleotides derived from the entire sequence of HPV39 and comprising at least 15 nucleotides and containing the highly conserved GRE element at the nucleotide 6367 and more particularly emphasized in FIG. 4. Finally, the invention relates more specifically to the 3 nucleotide sequences identified below:

Consensus: GGTACANNNTGTTCT (SEQ ID NO: 6)
HPV39 (NCR): TCTACATTTTATACT (SEQ ID NO: 7)
HPV39 (L1): GGGACAGTATGTTCT (SEQ ID NO: 8)

The invention also relates to all fragments, the sizes of which do not exceed those of the fragments previously defined, the former being characterized in that they hybridize with the latter under strict conditions (Tm −20° C.), particularly when the following conditions are used:

Hybridization is carried out at 42° C. in a solution containing: 50 mM of sodium phosphate buffer, pH=6.5; 5×

SSC (1× SSC=0.15M NaCl 0.015M Na citrate); 50% formamide; 200 ug/ml of yeast transfer RNA; 0.02% of Denhart solution.

Also forming part of the invention are the fragments belonging to the same types, in particular in that they exhibit percentages of cross hybridization higher than 50% with the fragments defined more specifically above.

The use of one or other of the sequences mentioned above or nucleic acids containing them are particularly suitable for constituting the hybridization probe which makes possible the detection of a papillomavirus DNA related to HPV39 in a biological sample.

Generally speaking, the invention thus also relates to any recombinant DNA containing the above-mentioned HPV-DNA or fragments of this HPV-DNA, in particular hybridization probes formed from these recombinant DNAs and specially adapted to the detection of an infection by HPV39 or by a variant or subtype of this papillomavirus. These probes may be either labelled themselves or modified at certain nucleotides, in particular for the purpose of coupling them directly or indirectly with a separate marker. It will be obvious that in such probes the parts foreign to the nucleotide sequence corresponding to the DNA of the papillomavirus are such that there is no risk of their hybridizing under stringent conditions with the other nucleic acids possibly contained in the sample tested for the possible presence of DNA of the corresponding papillomavirus or one of its variants.

The procedure according to the invention for the in vitro diagnosis, in a biological sample to be tested usually obtained from a human patient, of an infection by a papillomavirus capable of leading to or having led to a genital neoplasia, in particular a cervical, vulvar or penile cancer, is hence characterized by placing a probe such as that defined above in contact with the nucleic acid of this sample, made accessible to the probe beforehand where necessary, preferably under stringent conditions of hybridization, and by detection of the hybrid formed between the vital DNA under investigation and possibly present in the sample and the said probe.

Each of the probes according to the invention or the mixtures containing the above-mentioned probe can, in particular, be used as follows, it being naturally understood that the diagnostic tests described are not to be considered as limiting the conditions of use under which these probes or mixtures of probes may in fact be used.

In the example considered the purpose is to identify a HPV in a biopsy, in cells obtained by scratching of lessions or in biopsy sections fixed by means of the Carnoy mixture (ethanol, chloroform, acetic acid 6:3:1) and embedded in paraffin. The examination necessitates the prior extraction of the DNA from samples according to methods, the principle of which is known and involves the analysis of this DNA by molecular hybridization experiments carried out under stringent or less stringent conditions with the aid of radioactive probes (labelled with $^{32}p$ or $^{35}S$) prepared from the HPV according to the invention or mixtures of DNAs or HPVs containing it.

Several methods of hybridization may be used. It is possible, for example, to employ the dot method of hybridization. After denaturation of the DNA, this method comprises the deposition of aliquot amounts of DNA on membranes (nitrocellulose or "Genescreenplus"), the hybridization of each membrane under the usual conditions with a mixture of probes end the detection of the radioactive hybrids by exposure of the membranes to contact with a radiographic film. It is also possible to use the replica method of hybridization. This method comprises the electrophoretic separation of the DNA fragments obtained after treatment of the DNA with restriction enzymes in an agarose gel, the transfer of the fragments to membranes (nitrocellulose, "Genescreenplus") after alkaline denaturation and their hybridization under the usual conditions with the appropriate mixture of probes. The formation of radioactive hybrids is detected after exposure of the membranes to contact with a radiographic film.

The radioactive probes are constituted either by DNAS of HPVs labelled by the method of "nick translation" or by RNAs prepared by transcription of vital DNAs inserted in a vector, for example of the SP6 type. The use of radioactive probes has the advantage of high sensitivity but this does not exclude the use of non-radioactive probes, for example biotinylated probes capable of being recognized by antibodies either labelled themselves or which are themselves recognized by antibodies bearing an enzymatic, fluorescent or other type of label.

The invention also relates to competent cell cultures transformed with recombinant DNAs of the type indicated above, in particular those in which the nucleotide sequence corresponding to the DNA or the sequence of the DNA of HPV39 is placed under the control of transcription and regulatory elements for this nucleotide sequence in the said cell culture.

Consequently, the invention also relates to the products of expression of these recombinant DNAs in the corresponding competent cell hosts and the corresponding antibodies capable of being produced against these expression products.

Consequently, the invention relates to the polypeptides resulting in particular from the expression of the genes E1, E2, E4, E6,, E7, L1, L2 of the HPV39-DNA, respectively.

The procedure according to the invention for the production of these polypeptides consequently comprises the transformation of competent cell cultures with the recombinant DNAs containing the corresponding nucleotide sequences derived from HPV39, such that the nucleotide sequence corresponding to one of the said proteins can be expressed in this cell host, the recovery of these polypeptides from the products synthesized by the competent cell host and the purification (for example, by placing the expression products previously extracted from the cell cultures or from the medium in which the latter were grown in contact with antibodies previously formed against such peptides).

The expression products of the L2 sequences of each of the genomes of the papillomaviruses according to the invention have however a quite special value in that they may themselves be used for the in vivo production of antibodies capable of recognizing the expression products of the L2 gene in biological samples infected by a papillomavirus of the HPV39 type or by a variant of the latter, and more particularly when the preparations of the type in question have been fixed.

The invention also relates to hybrid polypeptides containing the above-mentioned polypeptides and derivatives respectively of HPV39, for example the L2 protein fused with other polypeptide sequences provided that the latter do not modify essentially the immunogenic properties of the L2 protein. The presence of these other polypeptide fragments may also result from the method used to produce these hybrid polypeptides, for example by means of genetic engineering. For example, these hybrid polypeptides contain a sequence derived from beta-galactosidase. Such products may be obtained in particular by transformation of *E. coli* with suitable vectors (phages or plasmids) modified by all or part of the lactose operon and containing, in addition, inserted downstream from the promoter of the lactose operon (or any other suitable promoter, for example of phage lambda), the nucleotide sequence derived from the L2 gene derived from HPV39. Recourse is advantageously had to plasmids or phages of this type comprising at least a part of the gene for the beta-galactosidase of the lactose operon.

When they have been purified, the polypeptides according to the invention may also be used in purification procedures for the antibodies which correspond to them, in particular from the sera of animals which had been immunised by these polypeptides. In particular, these polypeptides may be bound to affinity column. The steps entailed in the purification of the antibodies then consist of passing the serum containing them through affinity columns bearing the polypeptides mentioned above. The antibodies selectively bound to these columns can then be recovered by dissociation of the antigen-antibody complexes by means of a suitable buffer of sufficient ionic strength, for example an aqueous solution of a salt such as ammonium acetate. It is also possible to have recourse to acidified solutions.

The invention also relates to a procedure for the production of antibodies against the said polypeptides, in particular against the expression products of the genes E6, E7 or preferably L2 of HPV39, this procedure comprising the immunization of a suitable live host with the said polypeptides and the recovery of the antibodies formed from a serum of the immunized host, in particular by placing these sera in contact with the corresponding polypeptides in the purified state and the recovery of these antibodies from the antigen-antibody complexes formed.

In particular, the invention relates to the above-mentioned antibodies, purified beforehand, in combination with a suitable pharmaceutical vehicle. This composition is then capable of being used for the treatment of the infection concerned, provided that the latter has been clinically diagnosed as the result of an in vitro diagnostic assay on a histological or cytological specimen taken from a patient. This composition (in particular in the form of a serum) may be administered preferably by the parenteral route. This serum is then capable of causing a regression of the infections induced by papillomaviruses of the HPV39 type.

These antibodies can be used more particularly in diagnostic assays of an infection due to HPV39 or to a related papillomavirus (or to a variant of this papillomavirus), provided that histological sections derived from infected persons also contain expression products of some of its structural genes, in particular L2.

Hence the invention also relates to a procedure of in vitro diagnosis of genital neoplasias, in particular of cervical, vulvar or penile cancers, comprising the placing of histopathological sections taken from lesions induced in the persons concerned under conditions leading to the production of an antigen-antibody complex and the detection of this antigen-antibody complex. Advantageously, the detection is performed on preparations fixed beforehand under dissociating conditions, for example with the Carnoy solution or mixture already mentioned above (also described in the monograph by L. LISON, entitled "Histochimie et cytochimie animales").

The anti-L2 antibodies possibly bound can be recognized by other antibodies formed against the former, these latter antibodies bearing suitable, preferably non-radioactive, markers. These markers are, for example, enzymatic or fluorescent in nature.

The antibodies thus selected, like the hybridization probes defined above to which they correspond, may consequently be used to diagnose in vitro the corresponding types of infections.

Finally, the invention relates to the corresponding vaccinating compositions containing one or preferably several other L2 proteins, in combination with a pharmaceutically acceptable vehicle suited to the selected mode of administration, particularly by the parenteral route. These compositions can be used to protect the persons subjected to high risks of infection by HPV39 or by papillomaviruses of a corresponding type.

TABLE 1

OPEN READING FRAMES (ORF)
THE STRAND SIMILAR TO THE mRNA OF THE HPV39 GENOME

| ORF | First nucleotide | First ATG | Nucleotide preceding the stop codon | ORF size (bp) | Molecular weight (kD) |
| --- | --- | --- | --- | --- | --- |
| E6 | 44 | 107 | 590 | 537 | 18.7 |
| E7 | 493 | 592 | 918 | 426 | 12.5 |
| E1 | 922 | 928 | 2168 | 1947 | 73.0 |
| E2 | 2780 | 2798 | 3907 | 1128 | 43.0 |
| E4 | 3393 | — | 3674 | 282 | — |
| E5 | 3958 | 3958 | 4173 | 216 | 9.0 |
| L2 | 4172 | 4250 | 5659 | 1488 | 49.9 |
| L1 | 5610 | 5643 | 7157 | 1548 | 56.0 |

TABLE 2

COMPARISON OF HPV PROTEINS WITH HPV39
(PERCENTAGES OF IDENTICAL AMINO ACIDS)

| | HPV18 | HPV33 | HPV16 | HPV11 | HPV8 |
| --- | --- | --- | --- | --- | --- |
| E6 | 68% | 51% | 48% | 38% | 26% |
| E1 | 71% | 55% | 48% | 51% | 40% |
| E2 | 53% | 47% | 49% | 47% | 33% |
| L2 | 71% | 53% | 56% | 50% | 37% |
| L1 | 77% | 66% | 65% | 65% | 54% | a The sequence comparisons were made by having recourse to a computer programme based on an algorithm of Needleman and Wunsch (41).

REFERENCES

1. De Villiers, E. J. Virol. 63, 4898–4903 (1989).
2. Seedorf, K., Krammer, G., Dürst, M., Suhia, S. and R oweicamp, W. G., Virology 145, 181–185 (1985).
3. Cole, S. T. and Danos. O., J. Mol. Biol. 193,599–608 (1987).
4. Goldsborough, M. D., DiSilvestre. D., Temple, G. F. and Lorincz. A. T., Virology 171, 306–311 (1989).
5. Beaudenon, S., Kremsdorf, D., Obalek. S., Jabioska, S., Pehau-Amauder, G., Croissant. O. and Orth, G., Virology 161, 374–384 (1987).
6. Danos, O., Katinka. M. and Yaniv, M., EMBO J. 1, 231–236 (1982).
7. Chen. E., Howley, P. M., Levinson, A. D., Seeburg, P.H., Nature 299, 529–534 (1982)
8. Darumann, K., Schwarz, E, Gissmann, L. and Zur Hausen, H., Virology 151, 124–130 (1986).
9. Fuchs, P. G., Iftner. T., Weninger, J. and Pfister. H., J. Virol. 58, 626–634 (1986).
10. Giri, I., Danos, O. and Yaniv, M., Proc. Natl. Acad. Sci. USA 82, 1580–1584 (1985).
11. Groff, D. E. and Lancaster, W. D., J. Virol. 56, 85–91 (1985).
12. Cole, S. T. and Streeck, R. E., J. Virol. 58, 991–995 (1986).
13. Schwarz, E., Dürst, M., Demankowski, C., Lattermann, O., Zech, R., Wolfsperger, E., Suhai, S. and Zur Hausen, H., EMBO J. 2, 2341–2348 (1983).

14. Zachow, K. R., Ostrow, R. S., Faras, A. J., Virology 158, 251–254 (1987).
15. Henikoff, S., Methods in Enzymology 155, 156–165 (1987).
16. Sanger, F., Nicklen, S. and Coulson, A. R., Proc. Natl. Acad. Sci. USA 74, 5463–5467 (1977).
17. Zhang, H., Scholl, R., Browse, J. and Somerville, C., Nucl. Acids. Res. 16, 1220 (1988).
18. Chow L. T., Nassen, M., Wolinsky, S. M. and Broker, T. R., J. Virol. 61, 2581–2588 (1987).
19. Engel, L. W., Heüman, C. A. and Howley, P. M., J. Virol. 47, 516–528 (1983).
20. Benoist, C. and Chambon, P., Nature 290, 304–310 (1983).
21. Wingender, E., Nucl. Acids Res. 16, 1879–1902 (1988).
22. Proudfoot, N., Nature 298, 516–517 (1982).
23. Spaiholz, B. A., Yang, Y. and Howley, P. M., Cell 42, 183–191 (1985).
24. Hirochika, H., Broker, T. R. and Chow, L. T., J. Virol. 61, 2599–2606 (1987).
25. Gloss, B., Chong, T. and Bernard, H.-U., J. Virol. 63, 1142–1152 (1989).
26. Thierry, F., Hezra, J. M., Danmann, K. and Yaniv, M., J. Virol. 61, 134–142 (1987).
27. Chan, W., Klock, G. and Bernard, H.-U., J. Virol. 63, 3261–3269 (1989).
28. Chin, M. T., Broker, T. R. and Chow, L. T., J. Virol. 63, 2967–2976 (1987).
29. Cripe, T. P., Haugen, T. H., Turk, J. P., Tabatabai, F., Schmid, P. G., Durst, M., Grissmann, L., Roman, A. and Turek, L. P., EMBO J. 6, 3745–3753 (1987).
30. Chong, T., Chan, W. K. and Bernard, H.-U., Nucl. Acids. Res. 18, 465–470 (1990).
31. Gloss, B., Yeo-Gioss, M., Meisteremst, M., Rogge, L., Winnacker, E. L. and Bernard, H.-U., Nucl. Acids. Res. 17, 3519–3533 (1989).
32. Angel, P., Imagawa, M., Chin R., Stein, B., Imbra, R. J., Rahmsdorf, H. J., Jonat, C., Herrlich, P. and Karin, M., Cell 49, 729–738 (1987).
33. Weiner, H., König, M. and Gruss, P., Science 219, 626–631 (1983).
34. Imagawa, M., Chin, R. and Karin, M., Cell 51, 251–258 (1987).
35. Smotkin, D., Prokoph, H. and Wettstein, F. O., J. Virol. 63, 1441–1447 (1989).
36. Smotkin, D. and Wettstein, F. O., Proc. Natl. Acad. Sci. USA 83, 4680–4684 (1986).
37. Munger, K., Phelps, W. C., Bubb, V., Howiey, P. M. and Schiegel, R., J. Virol. 63, 4417–4421 (1989).
38. Evans, R. M. and Hollenberg, S. M., Cell 52, 1–3 (1988).
39. Edmonds, C. and Vousden, K. H., J. Virol. 63, 2650–2656 (1989).
40. Figge, J. and Smith, T. F., Nature 334, 109 (1988).
41. Needleman, S. B. and Wunsch, C. D., J. Mol. Biol. 48, 443–450 (1970).

---

We claim:

1. A purified polypeptide encoded by a gene of HPV39, wherein said gene is selected from the group consisting of E1, E2, E4, E6, E7, L1 and L2.

2. The polypeptide of claim 1, wherein said gene is the L1 gene.

3. The polypeptide of claim 1, wherein said gene is the L2 gene.

4. A purified polypeptide encoded by the L1 or L2 genes of HPH39.

5. A purified polypeptide encoded by a gene of HPV39 papillomavirus having the DNA sequence shown in FIG. 1 (SEQ ID NO: 9).

6. The polypeptide of claim 5, wherein said polypeptide is encoded by a fragment of DNA, and wherein said fragment has the nucleotide sequence of the large open reading frame (ORF) of 1.3 kb extending from nucleotide 2050 to nucleotide 776 of FIG. 1 (SEQ ID NO: 9).

7. The polypeptide of claim 5, wherein said polypeptide is encoded by a fragment of DNA, and wherein said fragment has the nucleotide sequence of the minor open reading frame (ORF) extending either from nucleotide 4204 to nucleotide 3875 or from nucleotide 4227 to nucleotide 3875.

8. A purified antibody directed against the polypeptide of claim 1.

9. A purified antibody directed against the polypeptide of claim 2.

10. A purified antibody directed against the polypeptide of claim 3.

11. A purified antibody directed against the polypeptide of claim 4.

12. A purified antibody directed against the polypeptide of claim 5.

13. A method for the in vitro detection in a biological sample to be tested of an infection due to a papillomavirus of the HPV39 type, wherein skid HPV39 comprises at least one antigen, said method comprising placing the antibody of claim 8 in contact with said biological sample, and detecting a complex of said antibody and antigen in said sample.

14. The method of claim 13, wherein said biological sample comprises a genital neoplasia.

15. The method of claim 14, wherein said genital neoplasia is selected from the group consisting of cervical, vulvar, and penile cancers.

16. A method for the in vitro detection in a biological sample to be tested of an infection due to a papillomavirus of the HPV39 type, wherein said HPV39 comprises at least one antigen, said method comprising placing the antibody of claim 9 in contact with said biological sample, and detecting a complex of said antibody and antigen in said sample.

17. The method of claim 16, wherein said biological sample comprises a genital neoplasia.

18. The method of claim 17, wherein said genital neoplasia is selected from the group consisting of cervical, vulvar, and penile cancers.

19. A method for the in vitro detection in a biological sample to be tested of an infection due to a papillomavirus of the HPV39 type, wherein said HPV39 comprises at least one antigen, said method comprising placing the antibody of claim 10 in contact with said biological sample, and detecting a complex of said antibody and antibody in said sample.

20. The method of claim 19, wherein said biological sample comprises a genital neoplasia.

21. The method of claim 20, wherein said genital neoplasia is selected from the group consisting of cervical, vulvar, and penile cancers.

22. A method for the in vitro detection in a biological sample to be tested of an infection due to a papillomavirus of the HPV39 type, wherein said HPV39 comprises at least one antigen, said method comprising placing the antibody of claim 11 in contact with said biological sample, and detecting a complex of said antibody and antigen in said sample.

23. The method of claim 22, wherein said biological sample comprises a genital neoplasia.

24. The method of claim 23, wherein said genital neoplasia is selected from the group consisting of cervical, vulvar, and penile cancers.

25. A method for the in vitro detection in a biological sample to be tested of an infection due to a papillomavirus of the HPV39 type, wherein said HPV39 comprises at least one antigen, said method comprising placing the antibody of claim 12 in contact with said biological sample, and detecting a complex of said antibody and antigen in said sample.

26. The method of claim 25, wherein said biological sample comprises a genital neoplasia.

27. The method of claim 26, wherein said genital neoplasia is selected from the group consisting of cervical, vulvar, and penile cancers.

* * * * *